United States Patent [19]

Clark et al.

[11] 4,393,716

[45] Jul. 19, 1983

[54] FIXTURE FOR ENVIRONMENTAL EXPOSURE OF STRUCTURAL MATERIALS UNDER COMPRESSION LOAD

[75] Inventors: Ronald K. Clark, Hampton; W. Barry Lisagor, Newport News, both of Va.

[73] Assignee: The United States of America as represented by the Administrator of the National Aeronautics and Space Administration, Washington, D.C.

[21] Appl. No.: 210,506

[22] Filed: Nov. 26, 1980

[51] Int. Cl.³ .......................... G01N 3/08; G01N 3/02; G01N 25/00
[52] U.S. Cl. ...................................... 73/818; 73/822; 73/856; 73/860; 374/51
[58] Field of Search ................ 73/856, 860, 790, 818, 73/822, 15.6, 859, 858, 857; 269/101, 219; 24/263 A

[56] References Cited

U.S. PATENT DOCUMENTS

| | | | |
|---|---|---|---|
| 753,015 | 2/1904 | Tretch | 73/856 |
| 2,333,646 | 11/1943 | Frankel | 24/263 A |
| 2,419,711 | 4/1947 | Dillon | 73/860 X |
| 2,461,256 | 2/1949 | Black | 24/263 A |
| 2,467,129 | 4/1949 | Huber | 73/15.6 |
| 2,499,981 | 3/1950 | Strobel | 24/263 A |
| 2,510,596 | 6/1950 | Murphy | 24/263 A |
| 2,689,037 | 9/1954 | Knapp | 24/263 A |
| 2,694,922 | 11/1954 | Vilella | 73/15.6 |
| 2,993,254 | 7/1961 | Larson | 24/263 A |
| 3,203,232 | 8/1965 | Lehnig, Jr. | 73/860 X |
| 3,218,057 | 11/1965 | Catlin | 24/263 A |
| 3,234,778 | 2/1966 | Kreglo, Jr. | 73/15.6 |
| 3,252,321 | 5/1966 | Pfann | 73/818 |
| 3,397,572 | 8/1968 | Stolz et al. | 73/856 X |
| 3,572,102 | 3/1971 | Baratta | 73/821 X |
| 4,073,185 | 2/1978 | Griffin | 73/859 X |
| 4,294,441 | 10/1981 | O'Banion et al. | 269/219 X |

FOREIGN PATENT DOCUMENTS

| | | | |
|---|---|---|---|
| 1903042 | 1/1968 | Fed. Rep. of Germany | 73/856 |
| 2529491 | 1/1977 | Fed. Rep. of Germany | 73/818 |
| 227659 | 9/1968 | U.S.S.R. | 73/856 |
| 372348 | 3/1973 | U.S.S.R. | 73/818 |

OTHER PUBLICATIONS

Speciman Grips Model 640.05 by MTS Division, Research Inc., P.O. Box 6112, Minn., Minn., 55424.

*Primary Examiner*—Stephen A. Kreitman
*Assistant Examiner*—David V. Carlson
*Attorney, Agent, or Firm*—Wallace J. Nelson; Howard J. Osborn; John R. Manning

[57] ABSTRACT

The present invention relates to a device for stressing a deformable material specimen. The apparatus consists of top plate 11 and bottom plate 12 sandwiching a guide cylinder 13. The specimen 14 is positioned on the bottom plate 12 and attached to a load piston 20 (FIG. 2). Force is applied through top plate 11 into guide cylinder 13. Once specimen 14 has been loaded, the stress is maintained by tightening tie bolt nuts 17.

3 Claims, 3 Drawing Figures

FIXTURE FOR ENVIRONMENTAL EXPOSURE OF STRUCTURAL MATERIALS UNDER COMPRESSION LOAD

ORIGIN OF THE INVENTION

The invention described herein was made by employees of the United States Government and may be used by or for the Government for governmental purposes without the payment of any royalties thereon or therefor.

BACKGROUND OF THE INVENTION

The present invention relates to a device for stressing a deformable material specimen and maintaining the load on the specimen after the stressing force has been removed.

Mechanical tests of a small specimen often are used to simulate the behavior of a material under conditions of its service usage. Materials used in the construction of vehicles and equipment for use in aerospace applications must be able to withstand both extreme compression loads and extreme fluctuations in environmental conditions. To test the qualities of various materials, it is necessary to be able to simultaneously stress the materials and subject the specimens, while under stress, to changes in environmental conditions.

PRIOR ART

The prior art devices for stressing material specimens are not suitable for tests involving exposure of the stressed material to extreme environmental conditions. The prior art devices, although adequate for producing compression load, are too large and complex to be efficiently useful in the study of environmental effects on the test material.

Thus, a need exists for an economical and compact device suitable for the simultaneous testing of material specimens under compression load and during exposure to extreme environmental fluctuations.

Accordingly, it is an object of the present invention to provide an apparatus which permits the simultaneous testing of the effects of compression load and environmental fluctuations on material specimens.

It is a further object of the present invention to provide an apparatus for stressing materials which is both compact and economical.

These and other objects are achieved by providing a specimen loading fixture of two plates sandwiching a guide cylinder and held together by two tie bolts. A material specimen is positioned within the guide cylinder and load is transmitted to the specimen by a load piston. Load is applied to the specimen by adjusting a loading bolt to a desired value; placing the fixture in a test machine; applying load to the fixture until the plates are secure against the guide cylinder; and tightening the tie bolt nuts to maintain the specimen at the load value.

BRIEF DESCRIPTION OF THE DRAWINGS

A more complete appreciation of the present invention and many of the attendant advantages thereof will be readily apparent as the same becomes better understood with reference to the following detailed description when considered in connection with the accompanying drawings wherein.

DETAILED DESCRIPTION OF THE INVENTION

Figure 1:
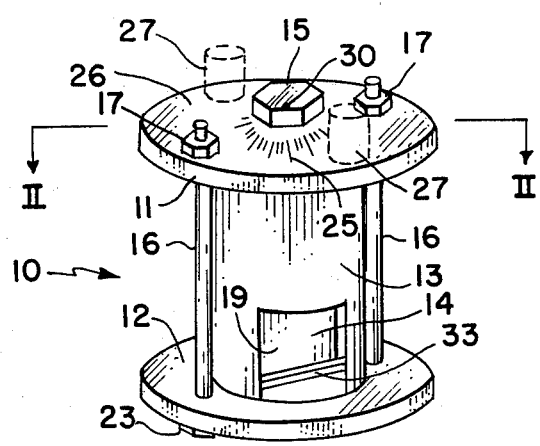
FIG. 1 is a side perspective view of the specimen loading fixture of the present invention.
Figure 2:
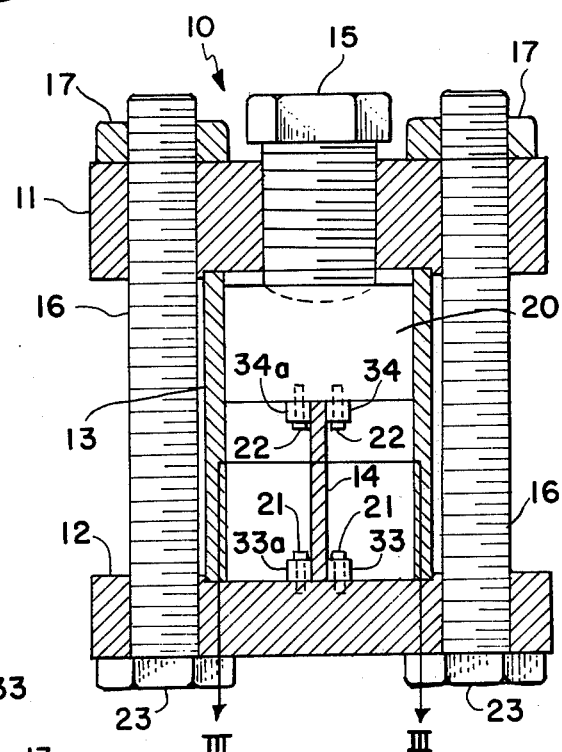
FIG. 2 is a sectional view of the specimen loading fixture shown in FIG. 1 and taken along line II—II thereof.

Referring now more particularly to FIG. 1, there is shown a loading fixture 10 comprising a top plate 11 and a bottom plate 12 sandwiching a guide cylinder 13. A load piston 20 (FIG. 2) is located within guide cylinder 13. A material test specimen 14 is secured to bottom plate 12 by retainers 33 and 33a. Specimen 14 is also secured by retainers 33 and 33a to load piston 20 (FIG. 2). Loading bolt 15 extends through the center of top plate 11 into guide cylinder 13 where it contacts load piston 20 (FIG. 2). Tie bolts 16 are provided with hex heads 23 and extend from bottom plate 12 to top plate 11 and are bolted on the upper surface of top plate 10 by tie bolt nuts 17. An area, indicated by reference numeral 19, of guide cylinder 13 is cut away near specimen 14 to permit exposure of the specimen to varying environmental conditions.

The positions of material test specimen 14 within guide cylinder 13 can be readily seen by reference to FIG. 2. Retainers 33 and 33a are attached to bottom plate 12 by screws 21. Retainers 34 and 34a are attached to load piston 20 by screws 22. Screws 21 and 22 fit into slots (32) in retainers 33, 33a, and in similar slots, not shown, in retainers 34 and 34a. When screws 21 and 22 are loosened, retainers 33, 33a, 34 and 34a are free to move in the slots either toward or away from specimen 14. To secure specimen 14, retainers 33, 33a, 34 and 34a are moved to snugly contact specimen 14 and screws 21 and 22 are tightened. Thus, loosening or tightening screws 21 and 22, retainers 33, 33a, and 34, 34a can be adjusted to accommodate varying specimen dimensions. As can be seen, guide cylinder 13 provides axial alignment for load piston 20.

Figure 3:
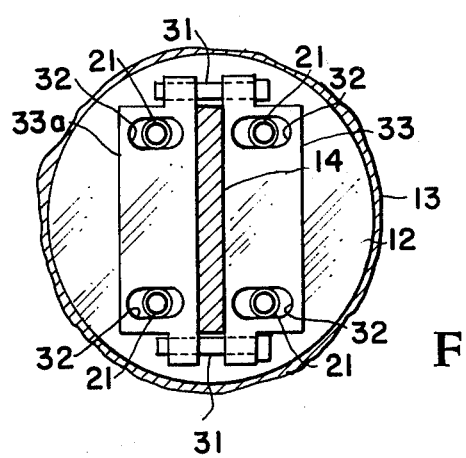
FIG. 3 is a view of the specimen loading fixture taken along line III—III of FIG. 2.

Referring now to FIG. 3, there is shown a top view of retainers 33 and 33a sandwiching specimen 14. Slots 32, approximately 0.3 inches in length, accommodate screws 21. Retainers 33 and 33a are free to move either toward or away from specimen 14. In assembly, retainers 33 and 33a are moved to contact specimen 14, screws 21 are tightened to secure retainers 33 and 33a to bottom plate 12. Screws 31 are tightened to secure retainer 33 to retainer 33a. Retainers 34 and 34a, are adjustable in like fashion and further description thereof is omitted herein in the interest of clarity.

OPERATION OF THE INVENTION

The operation of the present invention apparatus is now believed apparent. The calibrated loading fixture 10 and a specimen 14 are assembled, and retainers 33 and 34 are adjusted to assure axial loading of the specimen 14. The tie bolt nuts 17 are loosened, and the loading bolt 15 is adjusted to achieve the desired compression load by noting the angular position indicated by reference point 30 relative to reference lines 25 scribed on top plate 11. The tightening of tie bolt nuts 17 pushes top plate 11 and bottom plate 12 securely against guide cylinder 13 and concurrently pushes loading bolt 15 against load piston 20, thereby delivering the desired load to specimen 14. With the tie bolt nuts tightened, the load on the specimen will be maintained and the loading fixture can be placed in an environmental testing apparatus.

The calibration of the loading fixture is achieved by the following steps: (1) A gaged specimen is positioned in loading fixture 10. (2) Loading bolt 15 is loosened to clear load piston 20; tie bolt nuts 17 are tightened; and the loading bolt 15 is tightened to contact load piston 20. The angular position indicated by reference point 30 of loading bolt 15 is noted on the upper surface 26 of top plate 11 by reference lines 25 scribed on top plate 11. This represents the zero-load position. (3) Tie bolt nuts 17 are loosened and loading bolt 15 is advanced to the estimated position of the specimen target strain level. Tie bolt nuts 17 are tightened. (4) Loading fixture 10 is positioned in a test machine (not shown) which loads the fixture through bottom plate 12 and top plate 11. Loading force is applied to bottom plate 12 on the tie bolt heads 23. Loading force is applied to top plate 11 at points indicated by reference numeral 27. (5) Load/strain recording equipment (not shown) records specimen strain versus load. The loading fixture 10 is loaded to the estimated target strain level by the test machine. The tie bolt nuts 17 are tightened. The strain reading at this point is the strain locked in the specimen. Because the specimen is loaded through the fixture with the test machine and not by deflecting the loading bolt, no torque is applied to the specimen.

Although the invention has been described relative to a specific embodiment thereof, it is to be understood that numerous modifications may be made therein without departing from the spirit and scope of the instant invention. It is therefore to be understood that within the scope of the appended claims, the invention may be practiced otherwise than as specifically described herein.

What is claimed as new and desired to be secured by Letters Patent of the United States is:

1. An apparatus for stressing deformable materials which comprises:
   a top plate;
   a bottom plate;
   A guide cylinder positioned between said top plate and said bottom plate;
   a load piston positioned within said guide cylinder;
   an adjustable loading bolt positioned in the center and extending through said top plate to contact said load piston;
   means for positioning a deformable material specimen between said bottom plate and said load piston;
   said adjustable loading bolt serving to apply a compression load force to said load piston;
   means for maintaining the compression load force on said load piston, said means for maintaining the compression load force consisting of two tie bolts;
   each said tie bolt extending from the upper surface of said top plate to the lower surface of said bottom plate;
   said tie bolts being fixably attached to said bottom plate; and
   each of said tie bolts extending through a tie bolt nut positioned on the upper surface of said top plate;
   whereby tightening said tie bolt nuts draws said top plate toward said bottom plate, and pushes said top plate and said bottom plate securely against said guide cylinder to thereby maintain the compression load force applied to the specimen by said loading bolt and said load piston.

2. An apparatus as in claim 1 wherein said means for positioning a deformable material specimen between said bottom plate and said load piston comprises:
   adjustable retainers, each retainer having two slots with the lengthwise dimension of said slots oriented transverse to the lengthwise dimension of said retainer;
   two adjustable retainers connected to said bottom plate by first screw means inserted through said slots and with space between said retainers;
   two adjustable retainers connected to said load piston by second screw means inserted through said slots and with space between said retainers;
   whereby the deformable material specimen is positioned in the space between said retainers connected to said bottom plate and positioned in the space between said retainers connected to said load piston such that a clamping force is exerted on the deformable material specimen by loosening said first and said second screw means, moving said retainers to snugly contact the specimen and tightening both said first and said second screw means.

3. An apparatus as in claim 1 wherein said top plate has angular reference lines positioned around said adjustable loading bolt and wherein said adjustable loading bolt is provided with a reference point to facilitate the setting of the compression load force by said reference lines and said reference point.

* * * * *